United States Patent
Marcelpoil et al.

(10) Patent No.: US 12,421,488 B2
(45) Date of Patent: Sep. 23, 2025

(54) METHOD AND SYSTEM FOR LOCATING A BACTERIAL COLONY ON A CULTURE PLATE

(71) Applicant: BD KIESTRA B.V., Drachten (NL)

(72) Inventors: Raphael Rodolphe Marcelpoil, Corenc (FR); Martijn Kleefstra, Surhuisterveen (NL); Franciscus Feijen, Leeuwarden (NL); Jean-Marc Volle, Coublevie (FR); Mariska Okkema-Van Der Lei, Vrouwenparochie (NL); Gerard Mulder, Drachten (NL); Eelke Johannes Veeninga, Hantum (NL)

(73) Assignee: BD KIESTRA B.V., Drachten (NL)

( * ) Notice: Subject to any disclaimer, the term of this patent is extended or adjusted under 35 U.S.C. 154(b) by 897 days.

(21) Appl. No.: 17/621,008

(22) PCT Filed: Jun. 26, 2020

(86) PCT No.: PCT/EP2020/068100
§ 371 (c)(1),
(2) Date: Dec. 20, 2021

(87) PCT Pub. No.: WO2020/260634
PCT Pub. Date: Dec. 30, 2020

(65) Prior Publication Data
US 2022/0325225 A1 Oct. 13, 2022

Related U.S. Application Data

(60) Provisional application No. 62/867,560, filed on Jun. 27, 2019.

(51) Int. Cl.
*C12M 1/34* (2006.01)
*C12M 3/00* (2006.01)

(52) U.S. Cl.
CPC ............ *C12M 41/36* (2013.01); *C12M 23/48* (2013.01)

(58) Field of Classification Search
CPC ...... C12M 41/36; C12M 23/48; C12M 33/02; C12M 23/00; C12M 33/18; C12M 41/48; C12Q 1/04
See application file for complete search history.

(56) References Cited

U.S. PATENT DOCUMENTS

2012/0275681 A1 * 11/2012 Honda ................... C12M 33/00
382/133
2017/0260564 A1 9/2017 Lagarrigue-Charbonnier et al.

FOREIGN PATENT DOCUMENTS

CN 104403938 A 3/2015
CN 204264558 U 4/2015
(Continued)

OTHER PUBLICATIONS

International Search Report and Written Opinion issued in PCT application No. PCT/EP2020/068100 on Sep. 22, 2020, 10 pp.
(Continued)

*Primary Examiner* — John McGuirk
(74) *Attorney, Agent, or Firm* — Botos Churchill IP Law LLP

(57) ABSTRACT

An apparatus that configures a culture plate for precisely assigning coordinates to a selected colony by assigning fiducials to the culture plate using simple mechanical techniques. The fiducials correspond to the plate center and the center of a barcode label applied to the side of the culture plate by the apparatus. The apparatus then deploys mechanisms to apply coordinates to colonies identified by the user relative to the fiducials. One such mechanism is a webcam pointed at the culture plate that allows a technician to mark the colonies on a display using a computer mouse or equivalent cursor. Another mechanism deploys a laser (Continued)

pointer directed at the colony wherein the apparatus assigns coordinates to the location of the colony onto which the laser pointer is directed. In a third mechanism, the user views the surface of the culture plate through a viewfinder and manually registers coordinates when the view finder cross hairs are over a target colony. The selected colonies are assigned precise coordinates with reference to the two fiducials. Software is provided such that pixels in the image of the culture plate correspond to the coordinates of the culture dish relative to the fiducials.

21 Claims, 13 Drawing Sheets

(56) References Cited

FOREIGN PATENT DOCUMENTS

| CN | 205972927 | U | | 2/2017 | |
|----|-----------|---|---|--------|---|
| CN | 213537929 | U | | 6/2021 | |
| EP | 2497823 | A1 | | 9/2012 | |
| JP | 2000171360 | A | | 6/2000 | |
| JP | 2007308173 | A | | 11/2007 | |
| JP | 2011103779 | A | | 6/2011 | |
| JP | 2017202863 | A | * | 11/2017 | |
| JP | 2018523973 | A | | 8/2018 | |
| WO | WO-2016191646 | A2 | * | 12/2016 | C12M 33/04 |

OTHER PUBLICATIONS

Japanese Office Action issued in corresponding JP application No. 2021-577679 on Jul. 23, 2024.

The First Office Action for Chinese Patent Application No. 202080046462.0, Jan. 7, 2025, 25 Pages.

Second Office Action issued in corresponding Chinese Application No. 2020800464620 on Jul. 17, 2025, pp. 21.

* cited by examiner

METHOD AND SYSTEM FOR LOCATING A BACTERIAL COLONY ON A CULTURE PLATE

CROSS-REFERENCE TO RELATED APPLICATION

The present application is a national phase entry under 35 U.S.C. § 371 of International Application No. PCT/EP2020/068100, filed Jun. 26, 2020, published in English, which application claims the benefit of the U.S. Provisional Application No. 62/867,560, which was filed on Jun. 27, 2019 and is incorporated herein by reference.

BACKGROUND OF THE INVENTION

Products and samples are routinely tested for microbial contamination for a variety of reasons from determining if a patient is infected with a microorganism to determining whether food is contaminated with microorganisms. Because such testing is ubiquitous, large scale laboratories have been developed that can test hundreds or thousands of such samples. In order to provide laboratories with high throughput and lower overhead, these laboratories are becoming highly automated, to reduce the number of technicians needed to run such tests. One such automated platform is described in WO/2016/191646 entitled "Automated Method and System for Obtaining and Preparing Microorganism Sample for Both Identification and Antibiotic Susceptibility Tests" was published on Dec. 1, 2016 and is commonly assigned with the present application. Such a platform supports the goal of total lab automation (TLA) by providing work cell automation (WCA) of the functions performed by the automated platform. That application describes an automated system for preparing a picked portion of a colony of microorganisms for certain tests. The microorganism colonies are picked from a culture plate inoculated with a biological sample (e.g. a blood sample, a urine sample, a stool sample, a saliva sample, etc.). The inoculated culture plate is incubated to facilitate the growth of one or more colonies of microorganisms that may be present in the biological sample. The automated system locates the target colonies from the inoculated culture plate, then an automated pick tool moves to the location of the target colonies and picks the colonies. The automated system then prepares the picked colony for tests to determine the identity and the antibiotic susceptibility of the microorganisms that make up the colony.

Automated pick requires determining the coordinates of the target colony on the culture plate and communication of those coordinates to the picking tool to be used to obtain a portion of the colony from the culture plate. In fully automated systems, these coordinates can be obtained from a digital image of the culture plate from which the location of the target colony in the image is identified. These coordinates are provided by reference to fiducials provided with the culture plate. Such fiducials can be markings on the culture plate, markings in the culture media itself and a barcode located on the culture plate. Using a machine vision apparatus, another reference point such as the center of the dish is detected from which dish coordinates can be determined. The location of colonies on the dish can be determined in reference to their relative distance from the center and angular offset to the zero offset from one or more of the other fiducial markings. Once the relative location of the colony is determined, the dish can be moved to another system where the following two steps are performed. First, the dish is centered either manually or by mechanical means. The fiducial zero offset is detected, for example by rotating the dish while having a fixed sensor to detect the presence of the barcode label fiducial and scan the barcode with a barcode scanner. At this point the center of the dish is known and the barcode zero offset is known and therefore the location of the previously referenced colonies can easily be calculated as they are stored as distance to the dish center and angular offset to the barcode label.

The method as it is described above does not need a camera or computer vision system in the colony picking system, or any other system where the colony position information is required. The automated apparatus determines the coordinates from reference fiducials on the culture plate or applied by the user to identify the coordinates of the target colony in the coordinate space of the on the plate. However, such an apparatus requires determining colony coordinates from an image of the culture plate. Apparatus and methods for locating a colony on a culture dish without the need for a prior digital image to provide such location coordinates are therefore sought.

BRIEF SUMMARY OF THE INVENTION

Described herein is an apparatus that uses a simple mechanical arrangement that permits a user to either manually mark a target colony to associate the location of the colony in a coordinate space or to view an imaging device such as a webcam pointed at a culture plate and allow the user to mark or otherwise register the coordinates of the colonies on the plate viewed directly by the user of the displayed image of the plate via webcam. The marking of the colonies and the registry of those coordinates can be accomplished by a variety of mechanisms such as using a laser pointer either directly on the plate or onto an image of the plate to register colony coordinates or by moving a cursor over an image of the colony and clicking a mouse to register the coordinates of the cursor (and hence to colony on which the cursor is overlaid). Therefore, the actual coordinates of the plate have to correspond to the coordinates in either the user view of the plate or the webcam picture of the plate. The coordinates are relative to two fiducials and each coordinate is captured relative to the respective fiducials. For example, one fiducial is the midpoint of a barcode label affixed to the side of the plate and a second fiducial is the midpoint of the plate. The apparatus applies barcode labels to the plate in a repeatable fashion so that the midpoint of each label on each culture plate is fixated. The apparatus determines the radius of the culture plate and an angle in radians. That angle is between two lines, the first being an imaginary line between two fiducials (e.g. a label and the center of the dish) and the second being a line from one of the fiducials (e.g. the center of the dish) and the colony location (i.e., the coordinates of the colony relative to the position of the fiducials). The tolerance of the placement of the colony pick tool is about ±1 mm. The small tolerance is required to prevent the picking tool from missing the colony or picking from an adjacent unmarked colony. The size of the colony largely determines the required placement accuracy of the picking tool. After the apparatus has centered the plate and placed the bar code on the dish at a fixed position, the apparatus determines the coordinates of the colony of interest. Those coordinates are then stored and saved in a memory or data base that is associated with or connected to the system in the apparatus that determines the coordinates of the target colony in the dish coordinate space. The diameter of plates that can be used in the apparatus described herein is about 85 mm to about 90 mm.

Once the apparatus has determined the location of the colony on the dish to be picked relative to the fiducial markings (i.e. the plate center and the label) the coordinates of the colony in the plate coordinate space are stored in a database. When the plate is loaded into an apparatus from which the colony will be picked (i.e. the picking tool hereinafter) the barcode on the plate is scanned and the coordinates of the colony to be picked are transferred to the picking tool (or to a user interface if the coordinates are to be communicated to a technician for a manual pick). After the coordinates are supplied to the picking tool or user interface, the picking tool is brought into contact with the marked colony and the colony is picked.

Described herein is an apparatus having a table on which is placed a dish clamp supported by the table, the dish clamp including a platform on which a culture dish is manually placed and a chuck for securing the culture dish on the platform. The table also includes a colony marking device including a viewfinder that allows a user to view a colony through the viewfinder and assign coordinates to the colony relative to at least two fiducial marks. The apparatus has a label dispenser. The label dispenser includes a wheel mount that receives a roll of substrate carrying a plurality of labels where the plurality of labels carry adhesive on an outside surface of the label not affixed to the substrate strip. The label dispenser also includes at least one tensioning roller that subjects the substrate strip drawn from the roll to tension. The label dispenser also includes a biased roller assembly that urges the roller into engagement with a backside of the substrate strip thereby urging the outside surface of a label that carries adhesive into contact with a side of the culture dish. The table also includes a processor that assigns coordinates of a selected colony relative to the label on the culture dish and a center of the culture dish.

The viewfinder includes an angled mirror and crosshairs in a focal plane of the viewfinder. The apparatus further includes a label sensor proximate the biased roller assembly, where the label sensor identifies an edge of the label carried by the substrate strip as a fiducial mark. A controller is communicatively coupled to the label sensor and the biased roller assembly. The biased roller assembly is biased in a first position away from the culture dish and urges the label carried by the substrate strip into contact with the culture dish when the label sensor detects the label. A memory is provided, where the memory stores coordinates of a selected colony relative to the label affixed to the culture dish. The memory stores a coordinate map of the culture dish. The coordinates in the map are in relation to the label on the culture dish and the center of the culture dish. The apparatus further includes an imaging device, where the imaging device obtains an image of the culture dish and a colony is selected from an image of the culture dish. A camera is one example of an imaging device. In one embodiment the image of the culture dish is provided on a touchscreen display or a point and click display.

The apparatus can be used in a method to assign coordinate locations to colonies of microorganisms on a culture plate. In one embodiment of the method, a culture dish is placed into a chuck for securing the culture dish to a table or platform. An imaging device, including an image sensor, is provided to capture an image of the culture dish placed on the platform where the imaging device is coupled to a display for displaying the image of the culture dish captured by the imaging device. The method includes dispensing a label onto the culture dish using a label dispenser. The label dispenser has a wheel mount that receives a roll of substrate strip carrying a plurality of labels. The plurality of labels carry adhesive on an outside surface of the label not affixed to the substrate strip. The label dispenser also includes at least one tensioning roller that subjects the substrate strip drawn from the roll to tension. The label dispenser also includes a biased roller assembly that urges the roller into engagement with a backside of the substrate strip thereby urging the outside surface of a label that carries adhesive into contact with a side of the culture dish. The method includes assigning coordinates of a colony selected from the display relative to the label on the culture dish and the center of the culture dish. The user selects the colony of interest on the display and a processor associates the user selection with a coordinates on the culture dish relative to the center of the dish and the edge of the label.

In one exemplary embodiment the imaging device is a webcam. The apparatus further includes an adjustable mounting arm supported by the table, the adjustable mounting arm including a holder that carries the webcam. The label dispenser can further include a label sensor proximate the biased roller assembly, where the label sensor detects an edge of the label carried by the substrate strip. The apparatus includes a controller that is communicatively coupled to the label sensor and the biased roller assembly. The biased roller assembly is biased in a first position away from the culture dish and urges the label carried by the substrate strip into contact with the culture dish when the label sensor detects the label.

DETAILED DESCRIPTION

Figure 1:
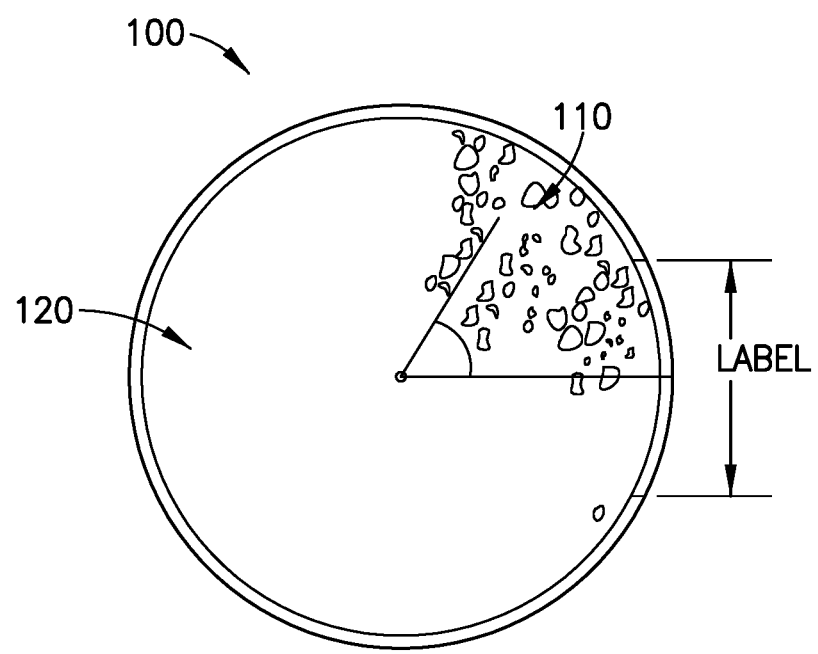
FIG. 1 illustrates a culture plate with colonies thereon and coordinate system with label and plate center fiducials.

Definitions of terms used in the specification.

| TERM | DEFINITION |
| --- | --- |
| AST | Antibiotic Susceptibility Testing: Susceptibility systems are utilized to determine what antimicrobials will be most effective in treating an infection by an organism. The organism is tested against various concentrations of antimicrobials, determining the organism's resistance (ineffective) or susceptibility (effective) to the antimicrobials. |
| ID | Identification: Identification systems are utilized to obtain the identification (genus and species) of an organism |
| MALDI-TOF MS | Matrix Assisted Laser Desorption Ionization-Time of Flight Mass Spectrometry |
| MIC | Minimal Inhibitory Concentration |
| Plate/Plated Media | Petri Dish/Petri Dish with Culture Media |
| ReadA Compact | The ReadA Compact is an intelligent incubation and imaging system that is commercially available from BD Kiestra ™ that stores, incubates and takes photographs of plated media. |
| Standalone | A standalone system described herein requires manual transfer of plated media into the infeed and out from the outfeed of the standalone apparatus. Upstream and downstream processing of the plated media processed by the standalone system described herein are performed outboard from the system described herein. |
| TLA | Total Lab Automation. Such systems enable automated specimen processing, plate incubation and digital imaging where workbenches are connected to the system and will offer integration of scalable automation modules such as, for example, BD Bruker ™ MALDI Biotyper ™ automated microorganism ID and the BD Phoenix ™ automated AST instruments. |
| WCA | Work Cell Automation, which is a modular solution designed for labs of all sizes that enables automated specimen processing, plate incubation and digital imaging in a compact footprint. |

Described herein is an apparatus that precisely indicates the location of microorganism colonies on a culture plate. As explained above, biological samples (e.g. animal fluids (e.g. blood, urine) and tissues, environmental samples (e.g. water, air), food samples, etc.) are often evaluated to determine if the samples are contaminated or, in the patient context, infected by micro-organisms (e.g. bacteria, virus, yeast, fungi, parasites). Typically, biological samples obtained from animal subjects are tested for bacterial infections.

Biological samples arrive at a testing laboratory in a variety of forms (fluids such as urine, blood, sputum, pus, feces, cerebrospinal fluid, etc.; tissue samples; etc.) and formats (sample tubes, swabs, etc.). The samples are inoculated onto culture media disposed in plates. The inoculated plates are then incubated, allowing time for microorganisms, if present in the sample, to grow. An incubated culture plate 100, is illustrated in FIG. 1A. The culture plate has microbial colonies 110 growing on the culture media 120.

BD Kiestra™ InoqulA™ automates the processing of both liquid and non-liquid bacteriology specimens to help streamline workflow, enable standardized processes and ensure consistent and high-quality streaking for inoculation of solid growth media 120. A culture media is inoculated with sample by any conventional means, such as depositing sample on the media and traversing the surface of the media with a magnetically controlled metal ball. Methods for inoculating sample onto media are well known to those skilled in the art and are not described in detail herein. Different inoculation patterns are used for different kind of samples.

After the colony 110 has grown to a sufficient size to provide an adequate amount of the colony for downstream testing, the colony is picked from the culture plate. While this may seem a rather straightforward task for a laboratory technician, manual colony pick is actually quite difficult as it requires precision to pick the exact colony. Consequently, the pick can be subject to errors and is certainly time-consuming. Therefore, automating such processes is beneficial because it requires less human labor and improves accuracy and efficiency. However, automating the colony locating process can be expensive since expensive imaging apparatus and software are required. The colony locating information, once, obtained, is shared with other apparatus that will actually acquire a portion of the colony from the plate. This requires the imaging apparatus to not only identify a colony to be picked, but to convey the location of the target colonies to the automated apparatus that will acquire the colony from the culture plate. As noted above, some laboratories do not have the benefit of imaging apparatus and software that obtains an image of the culture plate, evaluates the image and identifies target colonies in the image and the location of those target colonies in the coordinate space of the plate.

Since, in those systems, the colony coordinates are not provided from an image of the plated culture with the colonies thereon, the fiducials need to be present on the culture dish before the colonies are marked. In the embodiment where one of the fiducials is a label, that label is affixed using the apparatus described herein. The midpoint of the label is used along with the center of the plate to determine the radius and angle of the marked colony relative to these fiducials. In one embodiment, the apparatus fixes label on the side of the plate. In a further embodiment the apparatus has a store of labels to be placed on culture plates provided to the apparatus for colony marking since the colonies have not been marked from an image of the culture dish.

Prior to placing the label on the culture dish, the plate first has to be centered in the apparatus. One skilled in the art will appreciate that there are many different apparatuses that have a chuck that will center a circular article therein. One such apparatus is described in U.S. Ser. No. 62/697,197 filed on Jul. 12, 2018 entitled "Systems and Methods for Centering a Circular Object," which is commonly assigned with the present application and incorporated by reference herein.

Figure 2A:
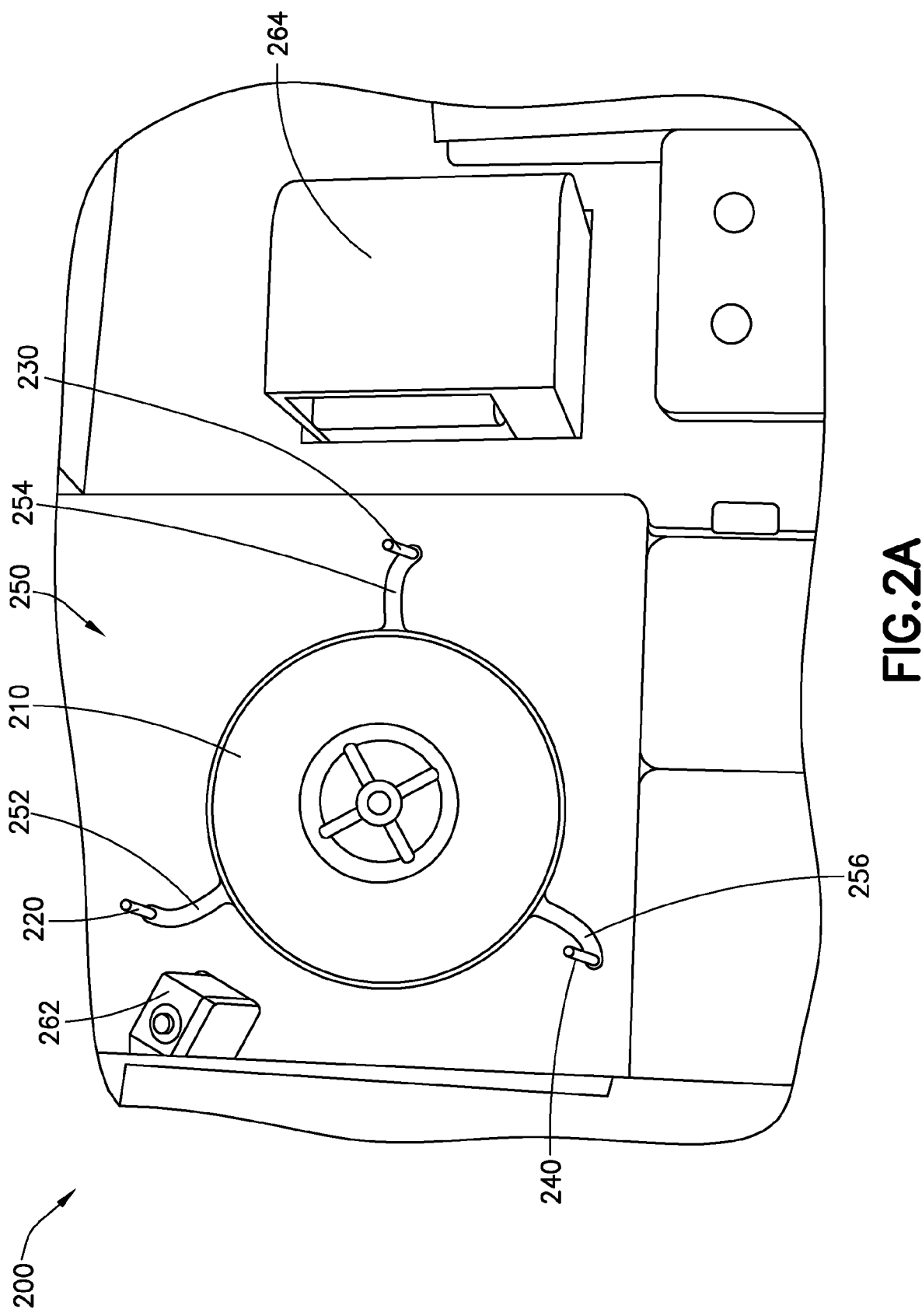
FIG. 2A illustrates an apparatus for centering a culture plate in an apparatus ether to select colonies or to pick colonies; exemplary embodiment of the apparatus described herein.
Figure 2B:
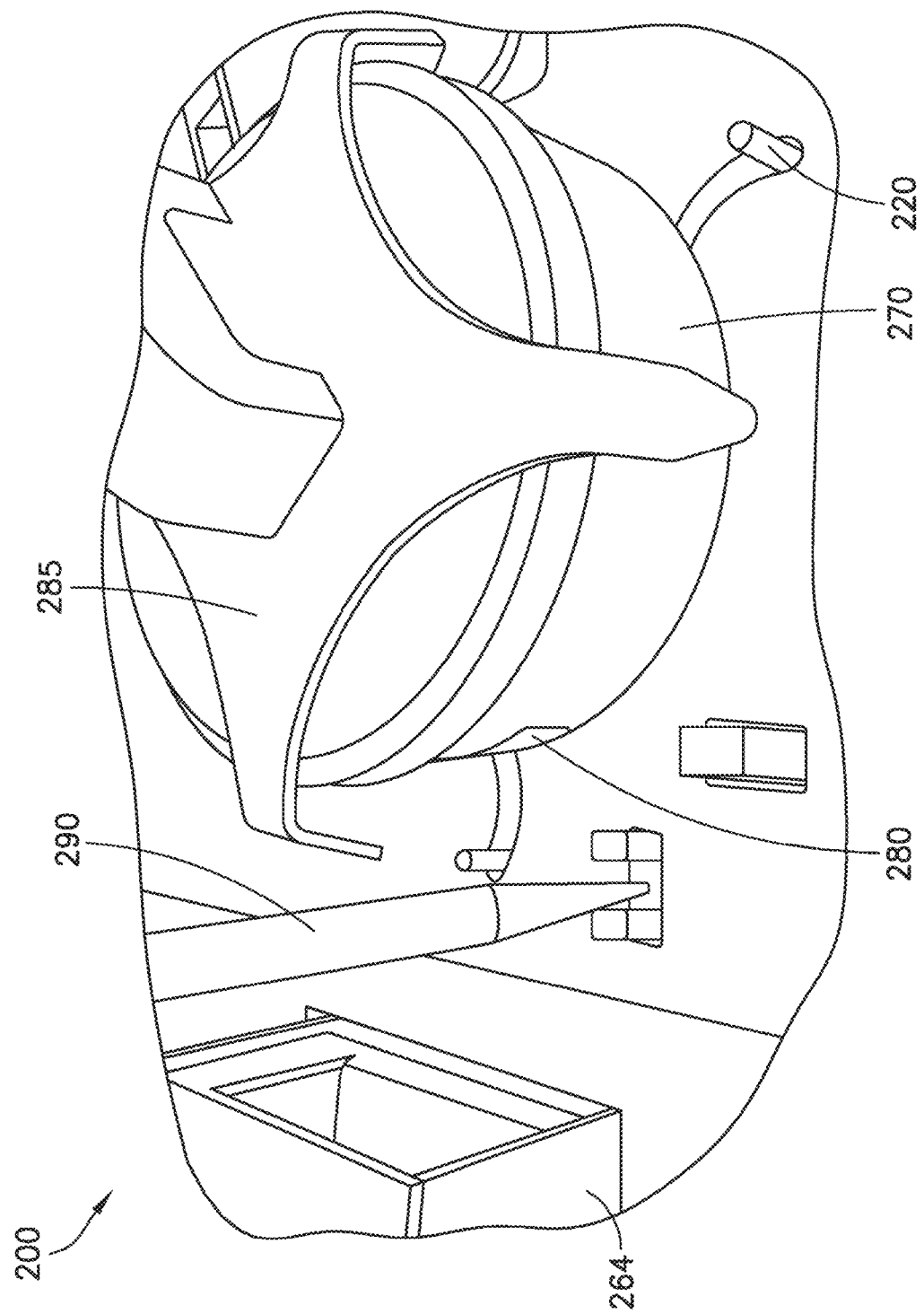
FIG. 2B is the apparatus of 2A with a culture plate being centered in the apparatus.

FIGS. 2(a)-(b) illustrate the system for centering a circular object described in U.S. Ser. No. 62/697,197. As shown, system 200 includes platform 210, pin 220, pin 230, pin 240, cover 250, sensor 262, reader 264, robot 285, and automated pipettor 290. Cover 250 includes slits 252, 254, and 256. Underneath cover 250, system 200 may include motors, pulleys, belts, and/or other components.

As shown in FIGS. 2(a)-(b), slits 252, 254, and 256 are curved and sized such that the diameters of slits 252, 254, and 256 correspond to the diameters of pins 210, 220, and 230. As a result, pins 220, 230 and 240 can traverse approximately the entire length of the slits 252, 254 and 256. Furthermore, in this embodiment, slits 252, 254, and 256 extend 15 millimeters away from platform 210. However, in other embodiments, the length of slits 252, 254, and 256 can be increased or decreased. For example, the lengths of slits 252, 254 and 256 can be selected to allow a petri dish to be placed onto platform 210 and rotated without substantial interference from pins 220, 230 and 240. As another example, the lengths of slits 252, 254 and 256 may significantly exceed (e.g., by a factor of two or more) the length required to allow a petri dish to be placed onto platform 210 and rotated without substantial interference from the 220, 230 and 240.

During a centering operation, slits 252, 254, and 256 guide pins 210, 220, and 230 as they are advanced toward platform 210. As shown, slits 252, 254, and 256 are curved and have a consistent diameter corresponding to the diameters of pins 210, 220, and 230. In other embodiments, slits 252, 254, and 256 may have different shapes. For example, slits 252, 254, and 256 may be generally straight and have a consistent diameter corresponding to the diameters of pins 210, 220, and 230. As another example, slits 252, 254, and 256 may have conical shapes with variable diameters. In such embodiments, slits 252, 254, and 256 may have narrow portions near platform 210 with diameters corresponding to the diameters of pins 210, 220, and 230.

As shown in FIG. 2(*b*), petri dish 270 can be placed on platform 210 by robot 285. Once on platform 210, pins 220, 230, and 240 may be used to center petri dish 270 on platform 210. After petri dish 270 has been centered, sensor 262 may also be used to orient petri dish 270. After petri dish 270 has been centered and oriented, reader 264 may be used to read a label 280 on petri dish 270. When the reader 264 measures a high contrast it interprets the high contrast as a label edge. From the location of the edge, the apparatus can determine the midpoint of the label 280, which is used as reference point for colony location as described elsewhere herein. By scanning the barcode, the module knows the coordinates and after positioning the plate correctly the colonies can be picked. Reader 264 may also be used to further orient petri dish 270. After petri dish 270 is centered and/or oriented, automated pipettor 290 may be used to pick one or more colonies of bacteria in petri dish 270.

Figure 3:
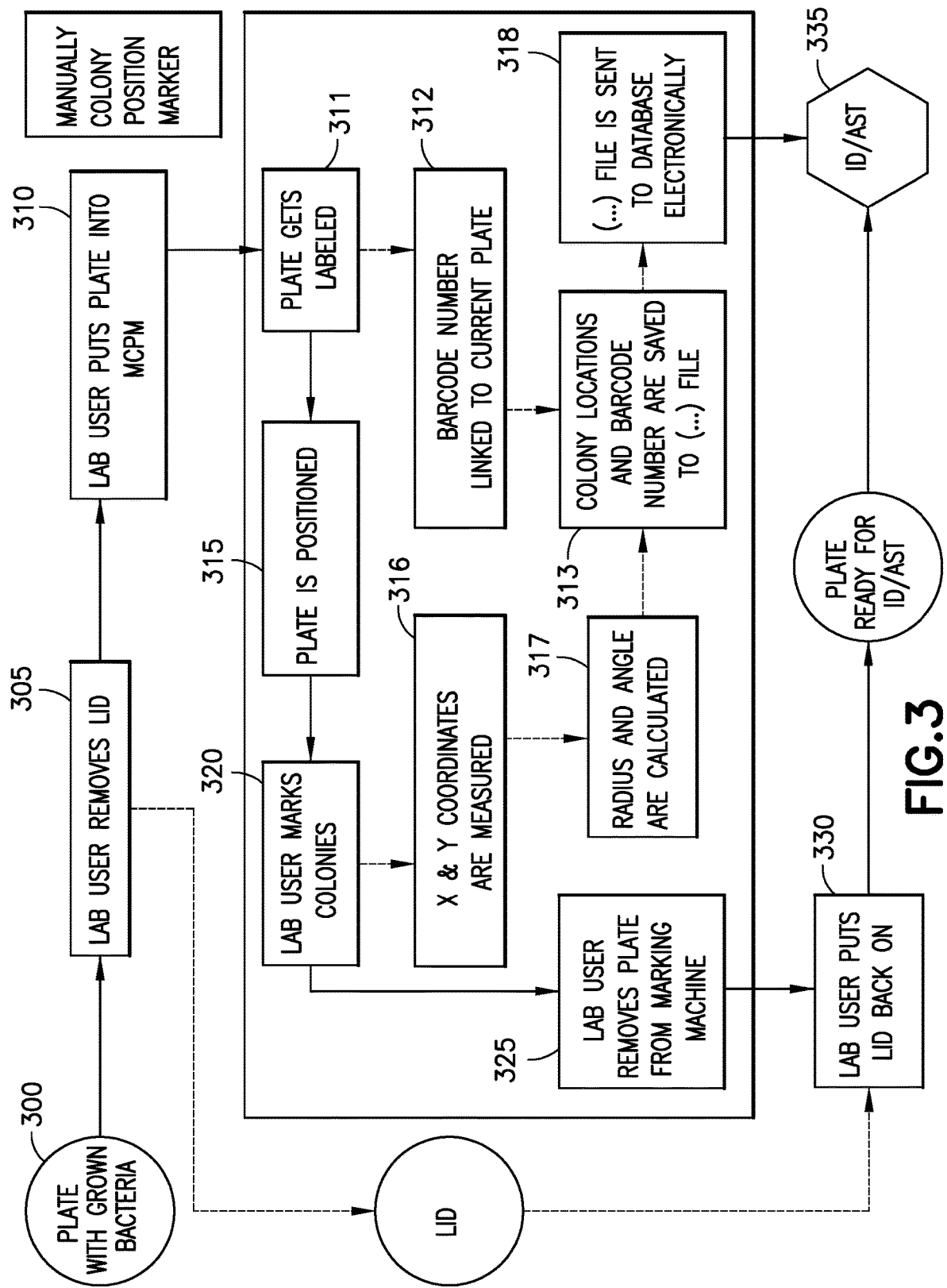
FIG. 3 is a flow chart for a method using the apparatus described herein.

One example of a manual method that uses the apparatus of the present invention is illustrated in FIG. 3. The above apparatus can be used to orient the petri dish for label placement thereon. The method begins with a plated culture, as illustrated in FIG. 1. The plated culture has been incubated and colonies of microorganisms have grown thereon in step 300. In step 305, the lid is removed from the culture dish and the lab user places the dish (with the lid thereon) in the apparatus described herein (step 310). When received by the apparatus, the dish is labeled (step 311). Labeling caused the barcode number be paired with the dish in the database that supports the apparatus (step 312). The barcode number is saved in a file that will be referenced once the colonies are picked and tested (step 313). After the plate is labeled, it is positioned (step 315) as described above. A technician either observes the plate in a first embodiment or a real time image of the plate (e.g. via webcam) in a second embodiment of step 320 and marks the colonies to be picked, at which time the x-y coordinates of the target colony is measured (step 316) and the radius and angle are calculated (step 317). The location of the colonies is combined with the barcode information (step 313) and the file with that information is sent to the database the supports the pick tool and any downstream testing (i.e. ID AST in step 335) of the picked colonies (step 318). In step 325, the technician removes the culture plate from the marking machine. In step 330, the technician replaces the lid on the culture dish after which the plate is ready to be used for ID/AST testing in step 335.

Using a dish clamp 710 (FIG. 7) and a label applicator 725 (FIG. 7) with a label detection sensor 760 (FIG. 12) enables the use of a simple mechanical and electrical method to generate the fiducials that provide coordinates for colony marking. The dish clamp generates the center fiducial and the label detection sensor generates the label (center) fiducial. When these two positions are determined, only the locations of the colonies need be determined. These colony locations can be marked in three ways.

In the first embodiment, the colony locations can be marked using a laser pointing device directed either at the surface of the culture dish or an image of the culture dish. One example of how a laser pointing device might be used to locate colonies is described in detail below.

Figure 14:
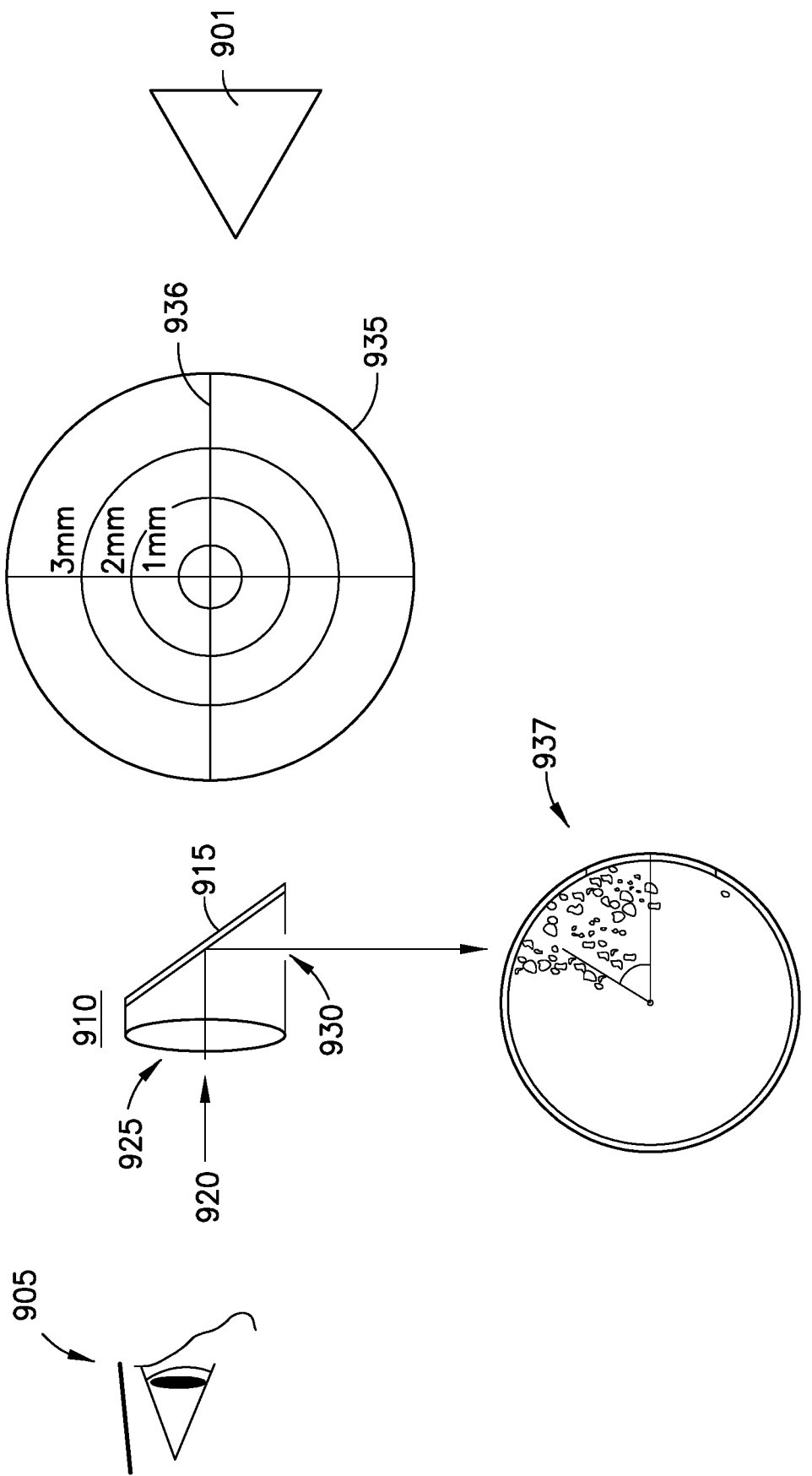
FIG. 14 illustrates an alternative embodiment for visual location of colony coordinates.

In a second embodiment, a view finder with crosshairs (i.e. a pair of fine wires or lines crossing at right angles in the focal plane) is used to assign the colony coordinates relative to the fiducials. This embodiment is illustrated in FIG. 14. In this embodiment, the view finder is used with an angled mirror (about forty-five (45) degrees in one embodiment) so that the user can look into the view-finder in a direction that is approximately parallel to the surface on which the colonies are located. The angled mirror re-orients the user's field of view approximately ninety (90) degrees so that the user can look into the viewfinder in an approximately horizontal direction and view the surface on which the colonies are located from a vertical perspective. As described in further detail below, the view finder is used to allow a user to manually view a colony and register its coordinates with reference to the plate center and label center fiducials. Registration of such coordinates can be achieved by, for example, using a laser pointer that registers the position of the beam in the coordinate space of the culture dish. When the user places the beam on the selected colony, the user can register the coordinates of that position relative to the fiducials using a button or switch provided to the user.

In a third instance, the user can locate the colony coordinates using a webcam. The use of webcam in this manner is described in detail below. In the embodiment wherein a webcam is deployed to locate colony coordinates, the need for computer vision to determine the plate center, barcode center or location of the colonies is eliminated. Eliminating the need for computer vision makes the device easier and simpler to set up. Also, when computer vision is not required, the system is not affected by surrounding light. Therefore, in the embodiments that do not require computer vision, the device does not need to be shielded from ambient light sources. When computer vision is not used, the possibility of software errors that might yield an incorrect location is eliminated. All of the interpretation of the image is done by the user. When computer vision is not used, the dish does not need to be shielded, and the user can still view the culture dish on which the colonies are located. This is advantageous because, if the user can view the dish when the fiducial markings are created, then the user can view the actual dish if the fiducial markings on the screen are not clear enough. The plate center and barcode center are determined mechanically and electronically as described above and coordinates are determined relative to those fiducials. When the webcam is used, the locations of the colony are determined by manual interpretation of the image and identifying target colonies that are then assigned coordinates relative to the fiducials.

Figure 4:
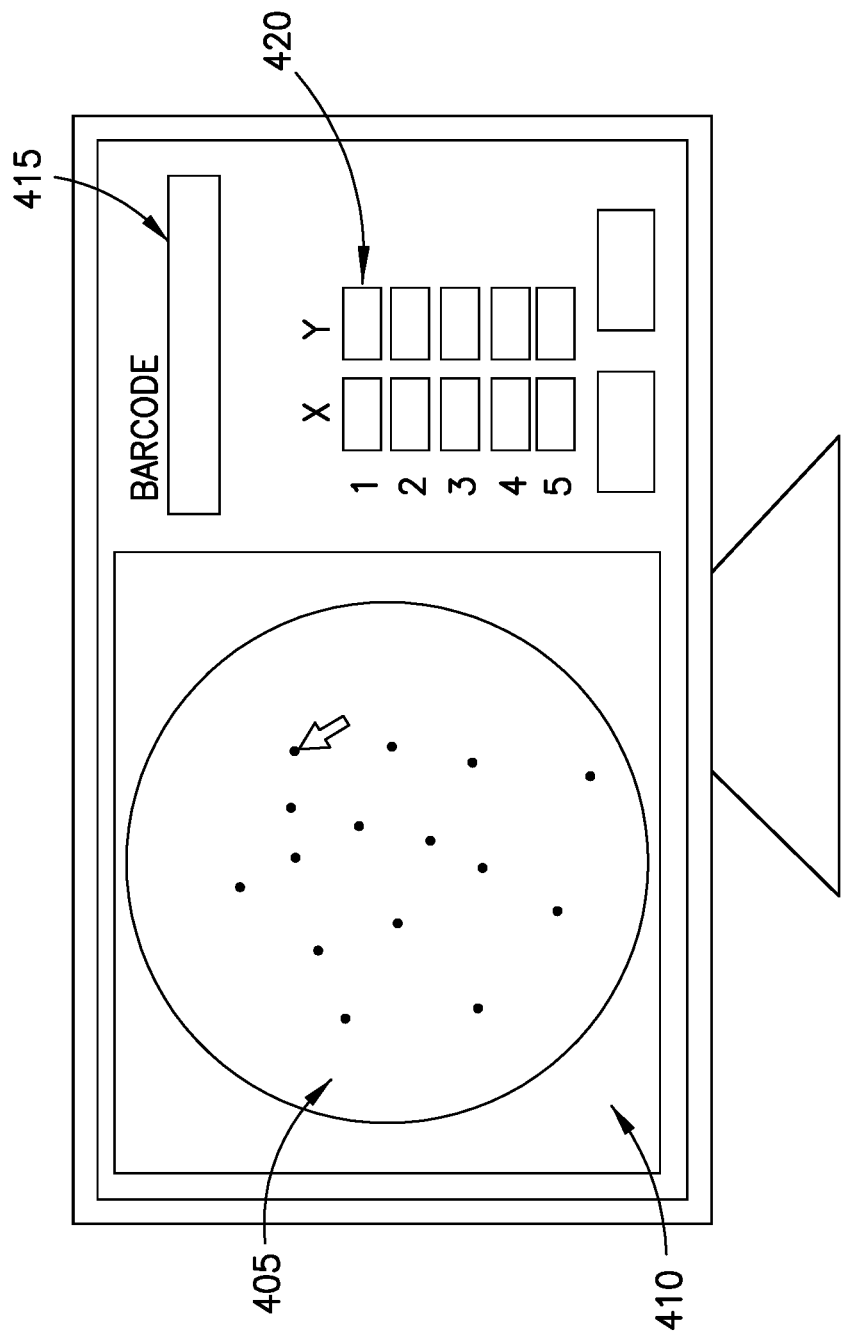
FIG. 4 is a monitor that displays a webcam image of a culture plate for colony selection.

One example of a webcam image of a culture plate with colonies formed thereon, that can be used by a technician to mark colonies of interest is illustrate in FIG. 4. FIG. 4 illustrates the image 405 of the culture dish viewed through display 410. The display 410 has a field 415 for the barcode, and fields for the x and y coordinates 420 of the colonies marked by the technician. One advantage to a webcam is that no laser or light beam need be directed at a colony of interest to mark it.

Laser beams and light beams are contemplated as alternative solutions to the webcam in the system described herein. For example, a laser pointing device is used to record the coordinates of a colony candidate. In this exemplary embodiment, the culture plate is placed in the marking machine as described herein. The marking machine centers the culture plate and rotates the label on the side of the culture dish to detect an edge(s) of the label (label 280 in FIG. 2(*b*)) on the side of the culture plate (petri dish 270 in FIG. 2(*b*)). Referring to FIG. 14, a pointer device 901 is used to manipulate a laser pointer to obtain coordinates of a target colony. The pointer device is either automated or controlled by a user 905. The pointer device cooperates with a view finder 910 that has a 45-degree mirror 915. Laser light or LED light 920 enters the pointer 910 through a first aperture 925 and is reflected downward, exiting pointer 910 through aperture 930 where it will be transmitted onto the surface of a culture plate 937. A view finder 910 having a target 935 with crosshairs 936 is provided with the pointer device for the user to orient the laser pointer in the coordinate space of the culture dish. Such view finders are well known to one skilled in art and are not described in detail herein. The view finder is provided with adjustable magnification for viewing the culture dish at the degree of magnification required to identify the colony of interest. The light beam is then directed at the colony and the coordinates where the light beam are incident on the culture dish are recorded. In a more manual operation, a user 905 can view the colonies through view finder 910. When viewing a colony of interest, the user can activate the laser to impinge on the colony of interest. Positioning the laser in this manner registers the coordinates at which the laser light impinges on the colony of interest. The light beam and the culture dish are capable of relative movement in x, y and z. As noted elsewhere herein, the culture dish is supported by a rotatable platform, so the culture dish can be rotated to place the target colony in a better position for marking its location. It should be noted that the coordinates of a particular pixel are fixed relative to the position of the label and the center of the dish. Rotating the culture dish does not change the coordinates of a given pixel in the culture dish coordinate space.

Figure 5:
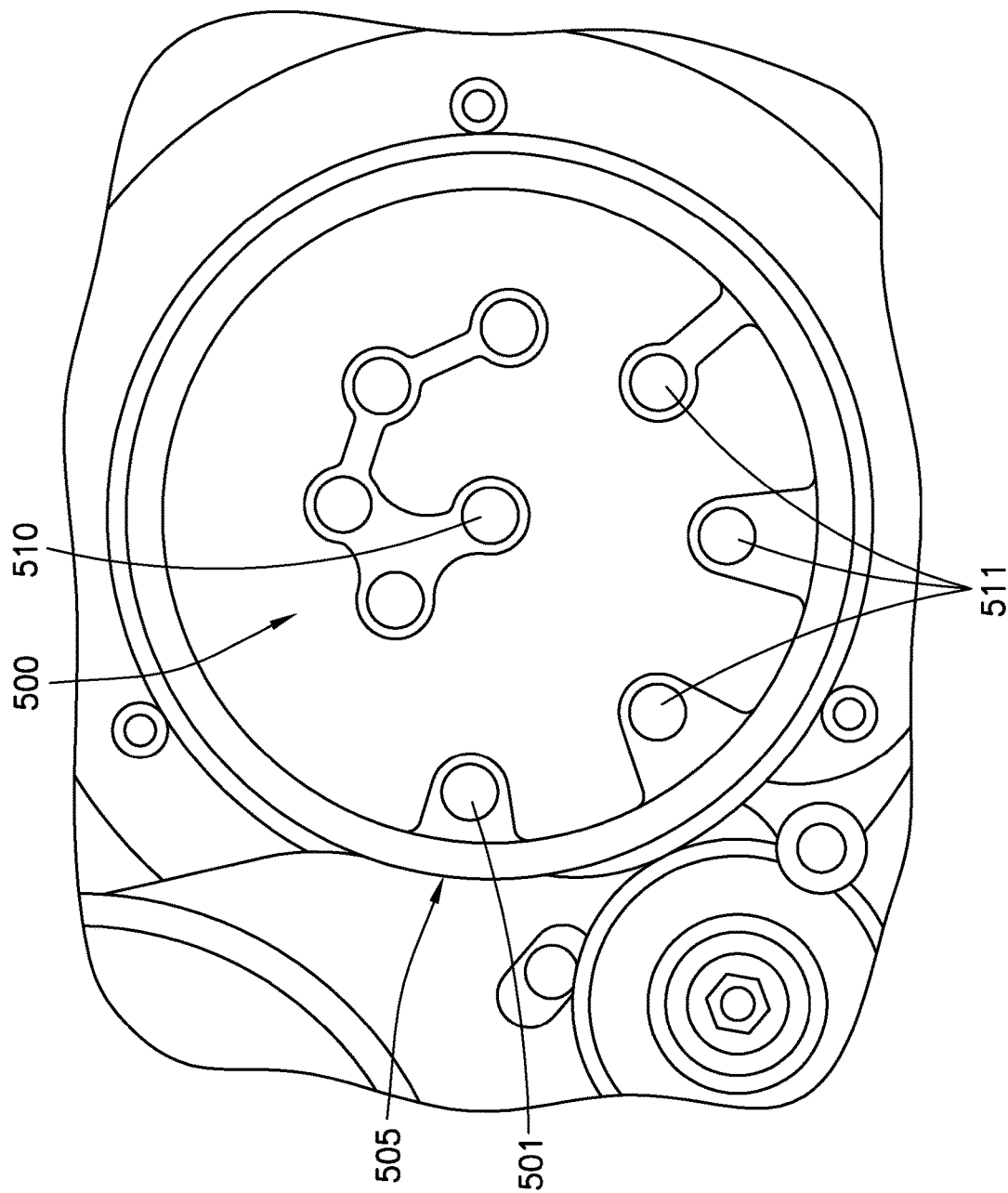
FIG. 5 is an apparatus for identifying colony coordinates using the center of the dish and the center of a label on the dish as fiducials.

In order to ensure correspondence between the coordinates of the marked colonies in the present apparatus with the coordinates used to pick the colonies for use in ID/AST, it is advantageous if the apparatus is calibrated. It is also advantageous if the apparatus is calibrated in the same manner as any other tools that may process the culture plate downstream of the apparatus described herein. In one embodiment, the downstream apparatus is an automated pick tool. One example of such a calibration dish 500 is illustrated in FIG. 5. The dish contains 9 reference points. Reference point 501 is midpoint of the label location 505 on the side of the dish. Reference point 510 is the center of the dish. The angle and radius of the remaining reference points 511 are known. The location software is calibrated using these points. This provides a map of the coordinate space of the culture dish and that coordinate space is saved in memory. When an image of a culture dish is displayed via webcam or display, the user selects the colony of interest and the coordinates of that colony are saved in memory relative to the culture plate fiducials (e.g. reference points 501 and 510). The coordinates of the colony can be obtained by the user in a variety of conventional ways. In one embodiment, a touchscreen is provided and the user can save the coordinates of interest by touching the touchscreen. In another embodiment, the user interface is a point and click monitor and the user can save the coordinates by hovering a cursor over the colony of interest and selecting that colony.

Since the apparatus links the coordinates of the marked colonies with the barcode of the label affixed to the culture plate in the apparatus, when the barcode of the plate is scanned when the dish enters the ID/AST module the ID/AST module knows where the marked colonies are located and can "find" them. ID is performed, for example, using MALDI-TOF MS. MALDI-TOF MS is a well-known apparatus for performing ID testing for microorganisms and is not described in detail herein. AST is a well-known technique for determining MIC of antibiotics against specific microorganisms. Systems and methods for AST are well-known to one skilled in the art and are not described in detail herein.

As noted above, the barcode is on the label affixed to the side of the culture plate before the colonies are marked by the technician using the apparatus. As noted above, the midpoint of the affixed label is used as one reference point for the radius and angle of the bacteria and the midpoint of the plate is used as a second such reference point. A user can supply the apparatus with a roll of labels with pre-printed barcodes. The apparatus is not required to print a barcode onto the labels (or onto the dish itself).

As noted above the apparatus can be used in conjunction with a mechanism (e.g. the above described webcam and display) that can assign coordinates to a colony of interest on the culture dish and can transmit those coordinates to an apparatus that will pick the colony of interest for testing. Automated pick tools are known to those skilled in the art and are not described in detail herein. In one example, an automated pick tool is integrated with automated apparatus that performs ID and AST testing. Such systems include a controller that communicates with the robotic pick tool, directing the robotic pick tool to acquire a pipette (or another suitable pick tool consumable such as a wire loop), and then carry the pipette or other pick tool to a location above the colony of interest. The top of the plate is removed prior to colony pick. The robotic pick tool then lowers the pipette or other consumable so that the consumable is in contact with the colony of interest.

In another embodiment, fiducial markings on the agar surface or on the culture dish can be used to orient the pick tool so that it acquires the target colony. These fiducial markings may be embedded on the plate during manufacturing, or applied by the user or by organic growth or incorporated on the dish or agar surface by any suitable means. Using a machine vision apparatus, another reference point such as the center of the dish is detected from which dish coordinates can be determined. As noted above, a barcode is one example of a fiducial. Also, as noted above, the location of colonies on the dish is determined in reference to their relative distance from the center and angular offset to the barcode zero offset. Once the relative location of the colony is determined by the apparatus described herein, the dish is moved to another system where the following two steps are performed. The dish is centered for example by mechanical means (such as the three-pin chuck described herein). The barcode zero offset is detected, for example by rotating the dish while having a fixed sensor to detect the presence of the barcode label and scan the barcode with a barcode scanner. At this point the center of the dish is known and the barcode zero offset is known and therefore the location of the previously referenced colonies can easily be calculated as they are stored as distance to the dish center and angular offset to the barcode label. The method and apparatus as described herein does not require a camera or computer vision system in the second system (colony picking system in this example), or any other system where the colony position information is required. The zero-offset used in this example is to the barcode label but it could be any unique fiducial feature of the dish or applied to the dish as noted above.

As noted above, once the colony coordinates in the plate coordinate space are determined by the apparatus, those coordinates are saved and communicated to an apparatus that will be used to pick the colony from the plate. The plate is transported to the apparatus in which the colony will be picked. One automated method and apparatus for picking up microorganisms from the surface of a culture medium is described in U.S. Pat. No. 9,677,044 entitled Method for Picking Up Cell Material and Assembly for Performing Said Method," to Botma et al. which is commonly owned and hereby incorporated by reference. One skilled in the art will appreciate that the method and apparatus described herein can be used to provide colony coordinates in the plate coordinate space to a variety of apparatus that can use the coordinates determined according to the apparatus and method described herein.

Figure 6:
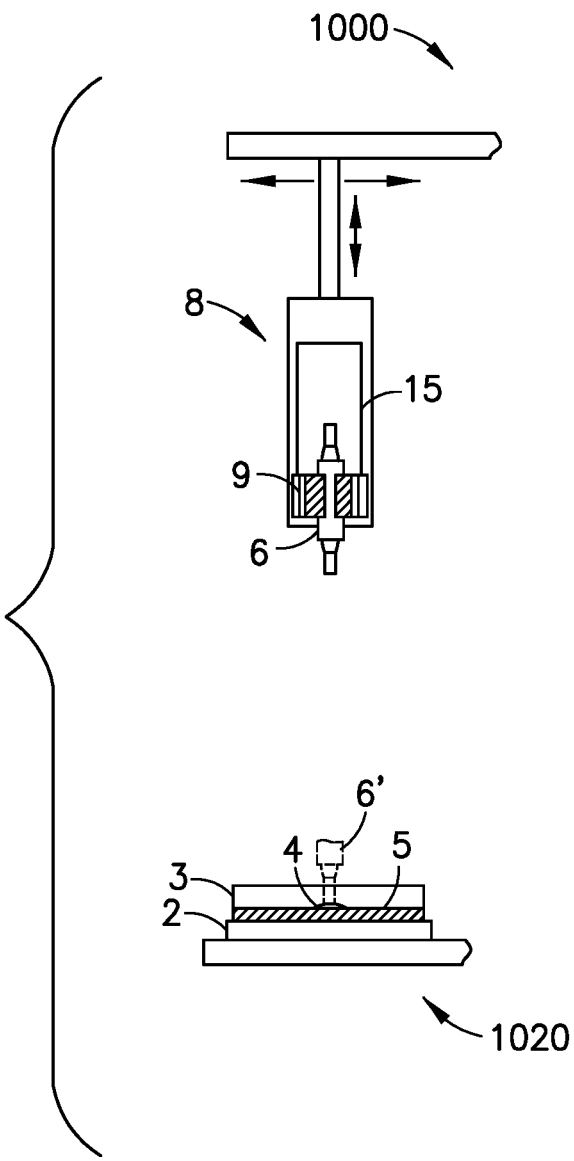
FIG. 6 illustrates a device that picks colonies from a plate with coordinates determined by the apparatus and method described herein.

Referring to FIG. 6, once dish 3 is received at pick station 1020, colony pick is performed. Station 1020 includes a positioning device 8 that comprises a pick tool holder 9 for releasably holding a pick tool, such as a disposable pipette tip. The positioning device receives coordinate information from the colony locating apparatus. The positioning device ascertains the location of the colony by first locating the fiducials that are the frame of reference for the colony coordinates. Then, the positioning device moves the pick tool over the dish to the coordinates identified by the colony locating apparatus. As shown, pick tool holder 9 holds a first pick tool 6. The positioning device 8 is arranged for positioning the first pick tool 6 in a starting position (shown in solid lines in FIG. 2) above the culture dish 3 and is arranged for automatically lowering and raising the first pick tool 6 towards and away from the culture dish 3, such that the first pick tool 6 can be positioned in a position (indicated with broken lines) in which it contacts the microorganism 4 and picks up a sample 19 of the microorganism 4. After the first pick tool 6 has picked up a sample 19 (first pick tool with retained sample 19 indicated in FIG. 2 as 6'), the positioning device 8 raises and positions the first pick tool 6' in a transfer position "A" located over a suspension tube 11. Positioning device 8 preferably raises pick tool 6' vertically to the starting position prior to moving horizontally along a transfer track 18 to the transfer location A. This may help prevent contamination by mucoid strings that may form during sample pick. However, in other embodiments positioning device 8 may move simultaneously both vertically and horizontally (as indicated by arrows in FIG. 2) toward the transfer position A.

Figure 7:
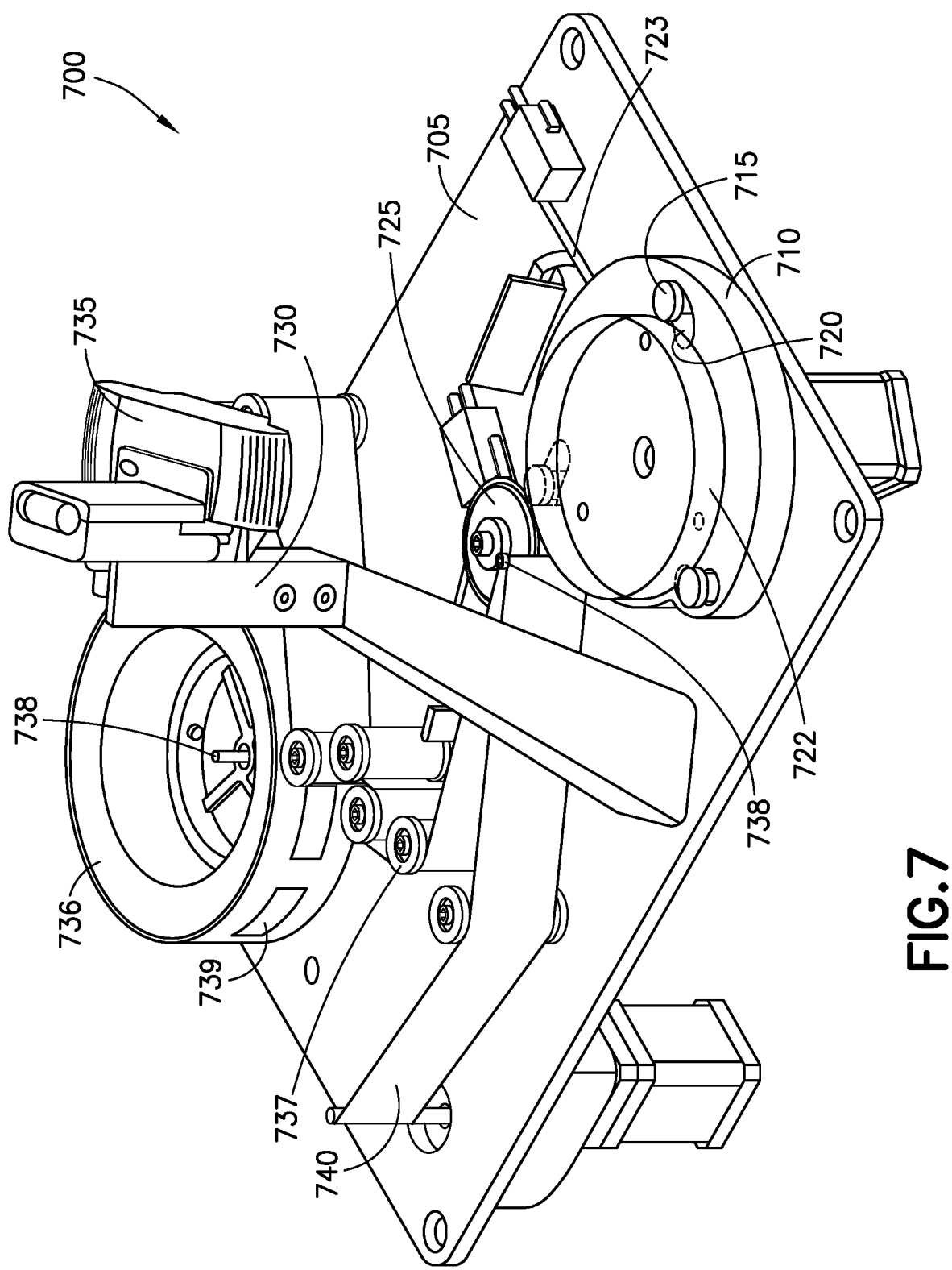
FIG. 7 is a perspective view of one embodiment of the apparatus described herein.

As noted above, the apparatus generates coordinates for the marked colony that reflect radius and angle in a reference coordinate space that corresponds with the coordinate space in which pick will occur. The apparatus deploys a table that can be moved in the x and y direction. Referring to FIG. 7, the apparatus 700, has a table 705 that can be adjusted in both the x and y directions. The apparatus 700 has a dish clamp 710 that uses three pins 715, each of which is opposed in a locking channel 720. The apparatus further includes a roller assembly 725 for attaching labels from a label strip 740 to the dish 722. A roll of the label strips 740 rotates around vertical axis 738 as the labels are advanced past a series of vertical rollers 737. The label strips 740 have an adhesive surface that carries labels 739. When the labels are advanced in proximity to the roller 725 at apex roller 738, the label 739, which has an adhesive on the outside, is moved into contact with the culture dish 722 by roller 725. The apparatus 700 also includes a webcam holder 730 with a webcam 735 mounted thereon.

Figure 8:
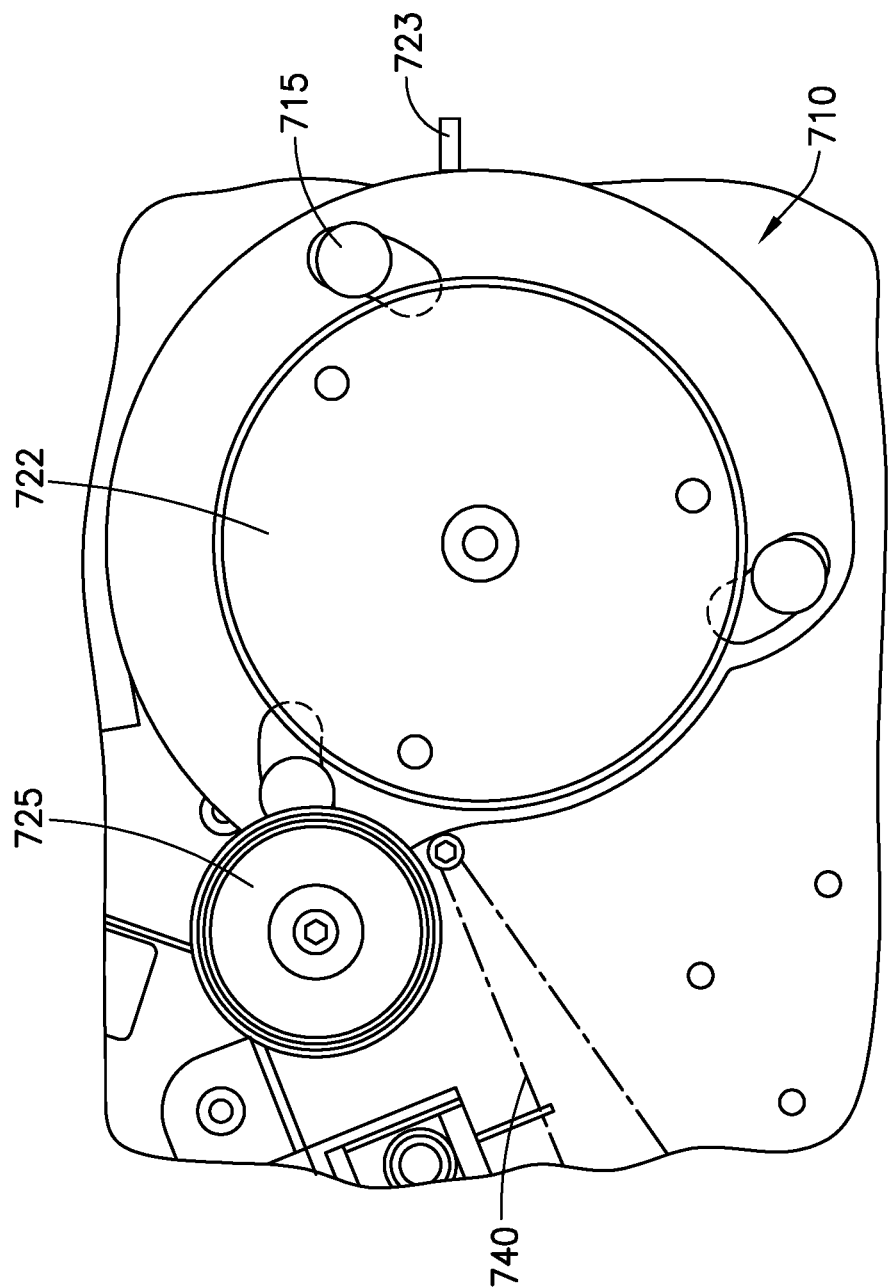
FIG. 8 is a top view of the disk claim of one embodiment of the present invention.

A top down view of the dish clamp 710 and roller 725 is illustrated in FIG. 8. In the illustrated position, the clamp is rotated such that the dish 722 is spaced away from the roller 725. When the pins 715 are in the illustrated position, the dish 722 is unlocked. When the pins 715 are in the locked position, the plate 722 is held in position as the roller 725 affixes a label from label strip 740 onto the dish 722. The pins 715 move from their first position to their second position by the pin 723. One of the three pins 715 is fixed to prevent the plate 722 from rotating on the clamping disc 710. The plate 722 is always fixed in the center of the clamping disc 710 because of the other two pins 715.

Figure 9:
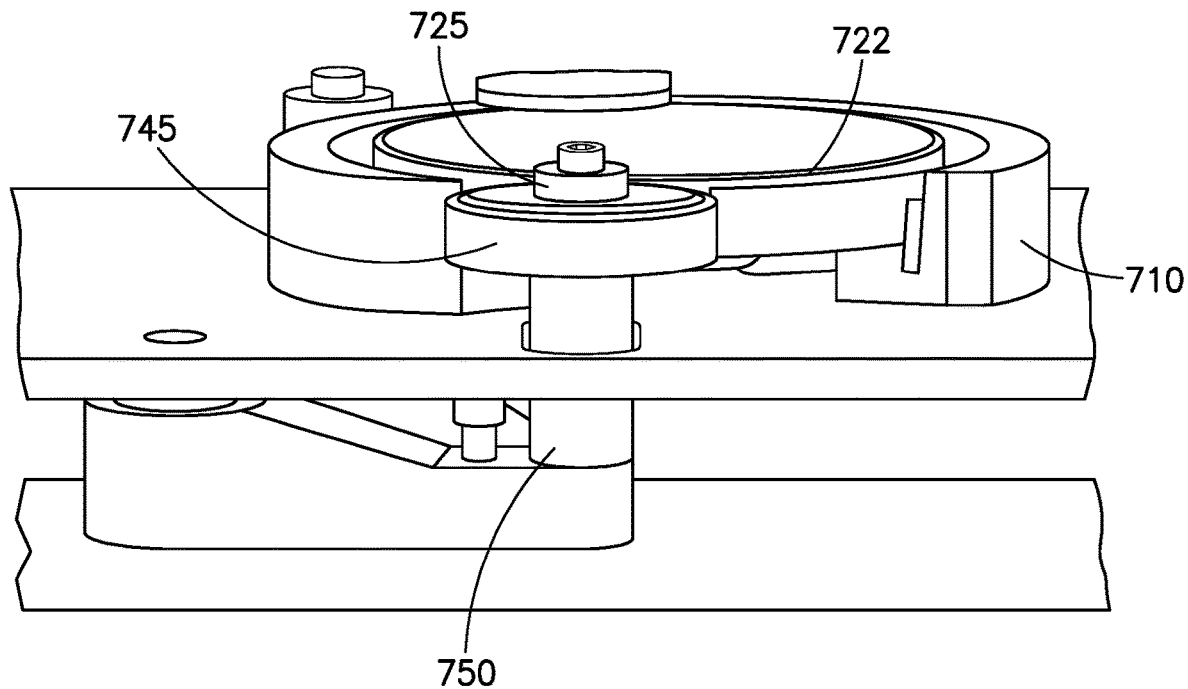
FIG. 9 is a perspective view of the roller assembly used to affix labels to the dish.
Figure 10:
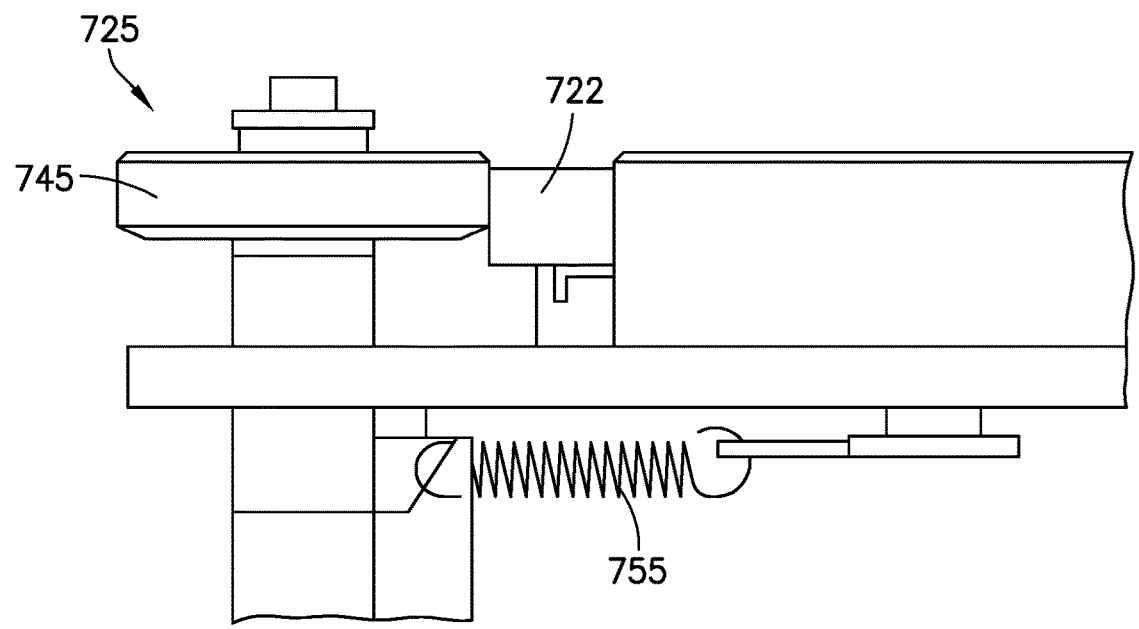
FIG. 10 is a side view of the roller assembly of FIG. 9, illustrating the spring used to draw the roller assembly and dish together for label transfer.

FIG. 9 is a side view of the roller assembly 725. The roller assembly 725 has a rubber roller wheel 745 disposed around bearing 750. The dish 722 is fixed in the clamp 710. As illustrated in FIG. 10, the roller assembly is biased close to the dish 722 by a spring 755. This causes the roller assembly to transfer a label from the strip of labels to the dish 722. Because the dish 722 typically has a conical shape (in which the bottom the dish has a slightly smaller diameter than the top of the dish such that the walls of the dish taper inward in the downward direction), the roller 725 tilts slightly outward commensurate in angle with the taper of the dish sidewall.

Figure 11:
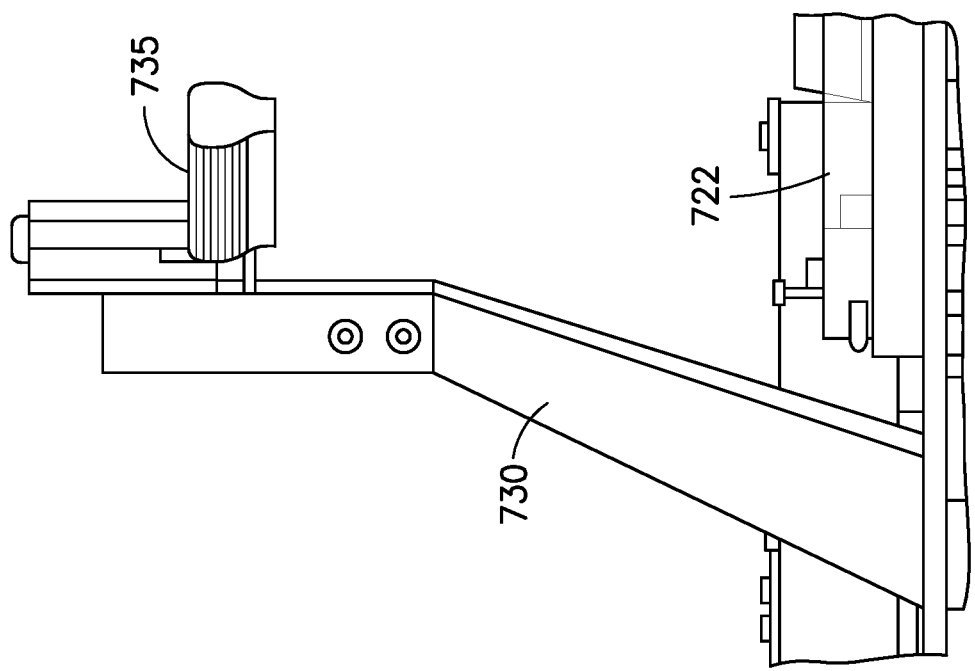
FIG. 11 illustrates the arm and the web cam used to obtain the image of the culture plate from which colonies, and colony coordinates, are established.

FIG. 11 illustrates the mounting arm 730 for the webcam 735 that transmits a real time image of the plated culture on plate 722. A technician uses the webcam image to select colonies to be picked. Because the dish 722 has been labeled. Coordinates are assigned to the selected colonies with reference to the midpoint of the applied label and the center of the dish 722.

Figure 12:
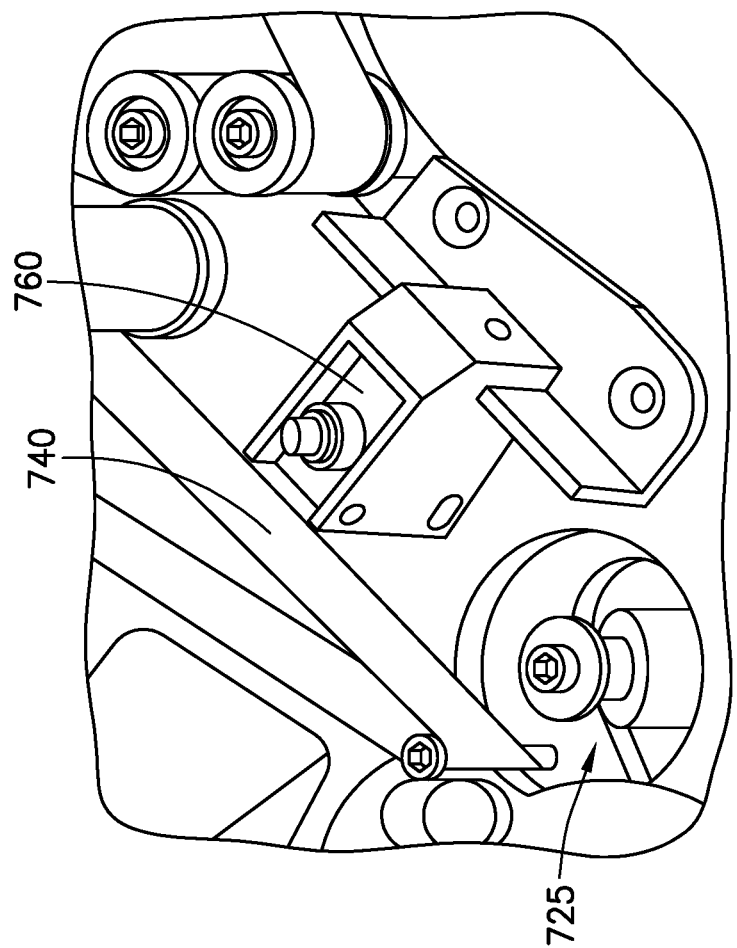
FIG. 12 illustrates a label sensor used to detect the label edge to determine when to transfer the label from the label strip to the dish.

FIG. 12 illustrates a sensor 760 that is used to detect a label on the strip of labels 740. The sensor detects the contrast between the label and its background. With the edge of the label detected, the roller assembly 725 and dish clamp 710 advance into contact to transfer the label from the label strip 740 to the dish 722.

Figure 13:
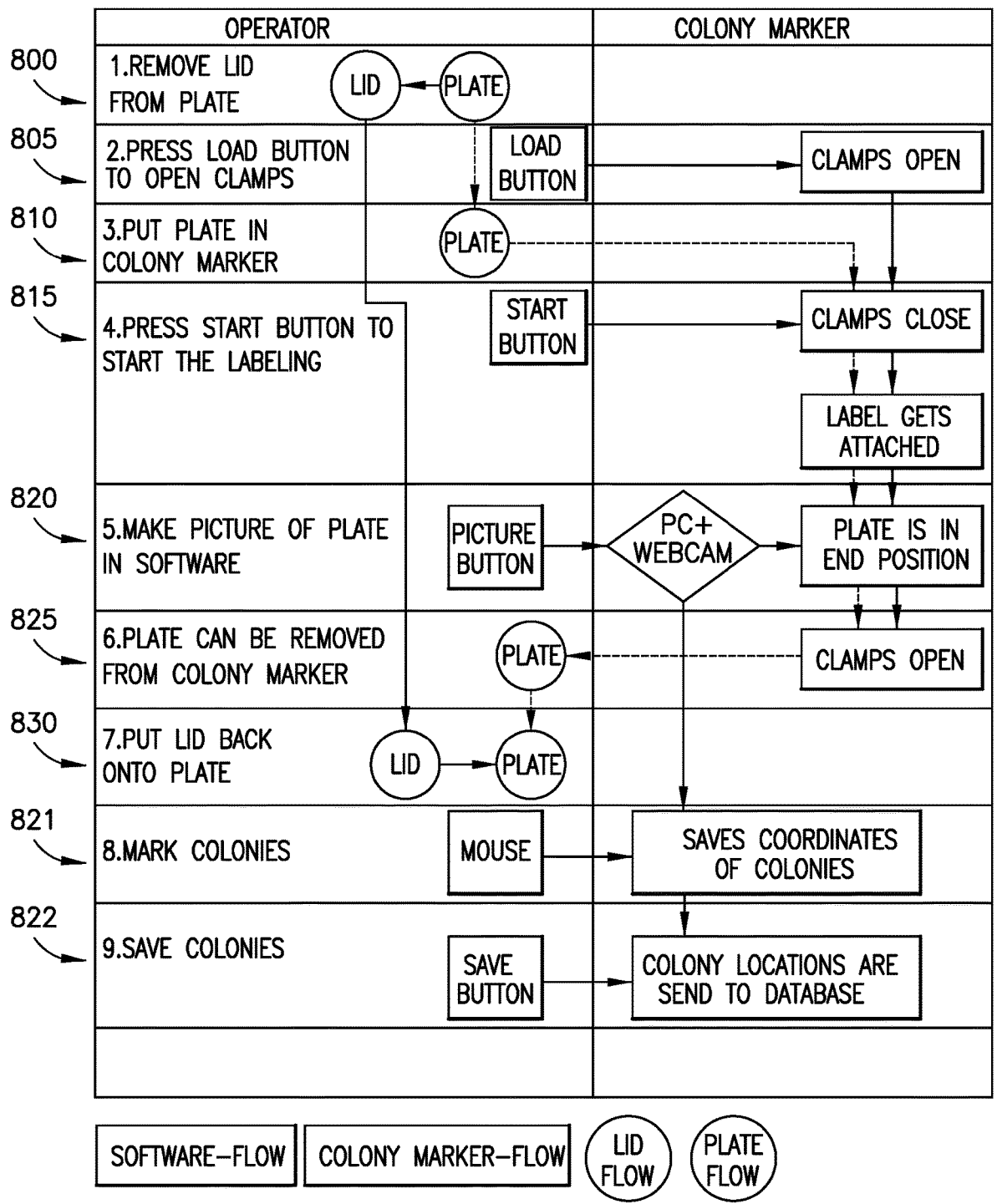
FIG. 13 is a flow chart for the operation of the apparatus described herein.

FIG. 13 is a flow chart for the operation of the apparatus describe herein. In step 800 the lid is removed from the plate. In step 805 the load button is pressed to place the clamp in the open position to receive the dish. In step 810 the dish is placed in the clamp. In step 815 the start switch is turned on and the clamp closes on the dish and the label is affixed. In step 820 the image of the plate is captured and the technician, in step 821, views and selects colonies, the coordinates of the selected colonies relative to the center of the label and the center of the dish are recorded in step 822. In step 825, the apparatus is turned off and the clamps open, permitting the technician to remove the plate from the apparatus. In step 830, the lid is placed back on the dish.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claim.

The invention claimed is:

1. An apparatus for assigning a coordinate location to a colony of microorganisms on a culture plate, the apparatus comprising:
   a table;
   a dish clamp supported by the table, the dish clamp comprising a platform on which a culture dish is manually placed and a chuck for securing the culture dish on the platform;
   a colony marking device comprising a viewfinder that allows a user to view a colony through the viewfinder and assign coordinates to the colony relative to at least two fiducial marks;
   a label dispenser comprising:
      a wheel mount that receives a roll of substrate strip carrying a plurality of labels wherein the plurality of labels carry adhesive on an outside surface of the label not affixed to the substrate strip;
      at least one tensioning roller that subjects the substrate strip drawn from the roll to tension;
      a biased roller assembly that urges the at least one tensioning roller into engagement with a backside of the substrate strip thereby urging the outside surface of a label that carries adhesive into contact with a side of the culture dish; and
      a processor that assigns coordinates of a selected colony relative to the label on the culture dish and a center of the culture dish.

2. The apparatus of claim 1, wherein the viewfinder comprises an angled mirror and crosshairs in a focal plane of the viewfinder.

3. The apparatus of claim 1, further comprising a label sensor proximate the biased roller assembly, wherein the label sensor identifies an edge of a label of the plurality of labels carried by the substrate strip as a fiducial mark.

4. The apparatus of claim 3, comprising a controller that is communicatively coupled to the label sensor and the biased roller assembly.

5. The apparatus of claim 4, wherein the biased roller assembly is biased in a first position away from the culture dish and urges the label carried by the substrate strip into contact with the culture dish when the label sensor detects the label.

6. The apparatus of claim 1, further comprising an imaging device, wherein the imaging device obtains an image of the culture dish and a colony is selected from an image of the culture dish, wherein the imaging device is a camera.

7. The apparatus of claim 1, wherein an image of the culture dish is provided on a display and the display is a touchscreen display.

8. The apparatus of claim 1, wherein an image of the culture dish is provided on a display and the display is a point and click display.

9. The apparatus of claim 1, further comprising a memory, wherein the memory stores coordinates of a selected colony relative to the label affixed to the culture dish.

10. The apparatus of claim 9, wherein the memory stores a coordinate map of the culture dish, the coordinate map in relation to the label on the culture dish and the center of the culture dish.

11. An apparatus for assigning a coordinate location to a colony of microorganisms on a culture plate, the apparatus comprising:
    a table;
    a dish clamp supported by the table, the dish clamp comprising a platform on which a culture dish is manually placed and a chuck for securing the culture dish on the platform;
    an imaging device comprising an image sensor, the imaging device placed to capture an image of the culture dish placed on the platform wherein the imaging device is coupled to a display for displaying the image of the culture dish captured by the imaging device;
    a label dispenser comprising:
       a wheel mount that receives a roll of substrate strip carrying a plurality of labels wherein the plurality of labels carry adhesive on an outside surface of the label not affixed to the substrate strip;
       at least one tensioning roller that subjects the substrate strip drawn from the roll to tension;
       a biased roller assembly that urges the at least one tensioning roller into engagement with a backside of the substrate strip thereby urging the outside surface of a label that carries adhesive into contact with a side of the culture dish; and
       a processor that assigns coordinates of a colony selected from the display relative to the label on the culture dish and a center of the culture dish.

12. The apparatus of claim 11, wherein the imaging device is a webcam.

13. The apparatus of claim 12, further comprising an adjustable mounting arm supported by the table, the adjustable mounting arm comprising a holder that carries the webcam.

14. The apparatus of claim 11, further comprising a label sensor proximate the biased roller assembly, wherein the label sensor identifies an edge of the label carried by the substrate strip as a fiducial mark.

15. The apparatus of claim 14, comprising a controller that is communicatively coupled to the label sensor and the biased roller assembly.

16. The apparatus of claim 15, wherein the biased roller assembly is biased in a first position away from the culture dish and urges the label carried by the substrate strip into contact with the culture dish when the label sensor detects the label.

17. The apparatus of claim 11, wherein the imaging device is a camera.

18. The apparatus of claim 11, wherein the display is a touchscreen display.

19. The apparatus of claim 11, wherein the display is a point and click display.

20. The apparatus of claim 11, further comprising a memory, wherein the memory stores coordinates of a selected colony relative to the label affixed to the culture dish.

21. The apparatus of claim 20, wherein the memory stores a coordinate map of the culture dish, the coordinate map in relation to the label on the culture dish and the center of the culture dish.

* * * * *